US008779360B2

(12) United States Patent
Miyake et al.

(10) Patent No.: US 8,779,360 B2
(45) Date of Patent: Jul. 15, 2014

(54) CHARGED PARTICLE BEAM DEVICE, DEFECT OBSERVATION DEVICE, AND MANAGEMENT SERVER

(75) Inventors: Kozo Miyake, Hitachinaka (JP); Junko Konishi, Hitachinaka (JP); Takehiro Hirai, Ushiku (JP); Kenji Obara, Kawasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/809,923

(22) PCT Filed: Jun. 22, 2011

(86) PCT No.: PCT/JP2011/003552
§ 371 (c)(1),
(2), (4) Date: Jan. 14, 2013

(87) PCT Pub. No.: WO2012/008096
PCT Pub. Date: Jan. 19, 2012

(65) Prior Publication Data
US 2013/0112893 A1 May 9, 2013

(30) Foreign Application Priority Data

Jul. 15, 2010 (JP) ................................ 2010-160193

(51) Int. Cl.
*H01J 37/153* (2006.01)
(52) U.S. Cl.
CPC .................................. *H01J 37/153* (2013.01)
USPC .......................................... 250/310; 250/306
(58) Field of Classification Search
USPC .......................................... 250/310, 306, 307
See application file for complete search history.

(56) References Cited

U.S. PATENT DOCUMENTS

| 8,355,559 B2* | 1/2013 | Harada et al. ................. 382/141 |
| 2003/0063123 A1 | 4/2003 | Fukube et al. |
| 2004/0044484 A1 | 3/2004 | Obara et al. |
| 2007/0272858 A1 | 11/2007 | Tanimoto et al. |
| 2011/0147587 A1 | 6/2011 | Yang et al. |
| 2013/0114881 A1* | 5/2013 | Harada et al. ................. 382/149 |

FOREIGN PATENT DOCUMENTS

| JP | 2004-153228 | 5/2004 |
| JP | 2006-108086 | 4/2006 |
| JP | 2006-128447 | 5/2006 |
| JP | 2007-265833 | 10/2007 |
| JP | 2010-87070 | 4/2010 |

* cited by examiner

*Primary Examiner* — Kiet T Nguyen
(74) *Attorney, Agent, or Firm* — Antonelli, Terry, Stout & Kraus, LLP.

(57) ABSTRACT

Provided is a charged particle beam device that prevents the increase in processing trouble caused by deterioration in the reviewing performance (e.g., overlooking of defects) by detecting an operation abnormality affecting the performance of the device or a possibility of such an abnormality in the middle of a processing sequence of a sample and giving a feedback in real time. In each processing step of the charged particle beam device, monitoring items representing the operating status of the device (control status of the electron beam, an offset amount at the time of wafer positioning, a defect coordinate error offset amount, etc.) are monitored during the processing sequence of a sample and stored as history information. In the middle of the processing sequence, a comparative judgment between the value of each monitoring item and the past history information corresponding to the monitoring item is made according to preset judgment criteria. When the width of fluctuation from the past history information deviates from a reference range, an alert is issued.

12 Claims, 16 Drawing Sheets

HIGH-MAGNIFICATION IMAGE ACQUISITION RATIO
= (n - m)/n×100 (%)

FIG. 6

| PROCESSING STEP | No | MONITORING CONTENTS | MONITORING ITEM | DETECTABLE ABNORMALITY |
|---|---|---|---|---|
| WAFER LOADING | 1 | ELECTRON BEAM CONTROL STATUS | FILAMENT CURRENT | SEM IMAGE QUALITY DETERIORATION, HARDWARE ABNORMALITY |
| | 2 | | PROBE CURRENT CONTROL VOLTAGE | |
| | 3 | | EXTRACTION VOLTAGE | |
| | 4 | | ACCELERATION VOLTAGE | |
| | 5 | | ELECTRON BEAM PATH CONTROL VOLTAGE | |
| WAFER ALIGNMENT | 9 | ALIGNMENT POINT DETECTION ACCURACY | OFFSET AMOUNT | DEFECT OFF VISUAL FIELD |
| | 10 | | ROTATION AMOUNT | |
| FINE ALIGNMENT | 11 | DEFECT COORDINATE DETECTION ACCURACY | OFFSET AMOUNT | DEFECT OFF VISUAL FIELD |
| | 12 | | ROTATION AMOUNT | |
| ADR (LOW-MAGNIFICATION IMAGE ACQUISITION) | 13 | DEFECT COORDINATE DETECTION ACCURACY | OFFSET AMOUNT | MISDETECTION AND OVERLOOKING OF DEFECT |
| | 14 | AUTOMATIC FOCUSING ACCURACY | EXCITATION CURRENT VARIATION | MISDETECTION AND OVERLOOKING OF DEFECT |
| ADR (HIGH-MAGNIFICATION IMAGE ACQUISITION) | 15 | AUTOMATIC FOCUSING ACCURACY | EXCITATION CURRENT VARIATION | IMAGE QUALITY DETERIORATION (BLURRED IMAGE) |
| | 16 | DEFECT DETECTION ACCURACY | HIGH-MAGNIFICATION IMAGE ACQUISITION RATIO | OVERLOOKING OF DEFECT |

FIG.12

```
                1201        1202            1203
2010_06_02_10:10:22 [RECIPE_START]                              ← RECIPE EXECUTION START
2010_06_02_10:10:25 [WF_LOAD]                                   ← SAMPLE CONVEYANCE START
2010_06_02_10:10:26 [WF_INFO]FMEM001,STIE,A0001,Slot01          ← SAMPLE INFORMATION
2010_06_02_10:10:27 [SEM_Con]1000,200                           ← ACCELERATION VOLTAGE, PROBE CURRENT
2010_06_02_10:10:28 [WA_START]                                  ← ALIGNMENT START
2010_06_02_10:10:30 [STAGE_MOVE]30000000,150000000              ← SAMPLE #1 STAGE MOVEMENT
2010_06_02_10:10:32 [MAG_SET]5000                               ← MAGNIFICATION SETTING
2010_06_02_10:10:35 [AF_INI]20000                               ← AUTOMATIC FOCUSING START POINT
2010_06_02_10:10:40 [AF_FIN]25000                               ← AUTOMATIC FOCUSING END POINT
2010_06_02_10:10:42 [WA_EXEC]1,0,30001500,150002500             ← ALIGNMENT RESULT
2010_06_02_10:10:55 [STAGE_MOVE]270000000,150000000             ← SAMPLE #2 STAGE MOVEMENT
                         .
                         .
                         .
2010_06_02_10:11:00 [ADR_START]                                 ← ADR START
2010_06_02_10:11:05 [STAGE_MOVE]:200000000,100000000            ← SAMPLE STAGE MOVEMENT
2010_06_02_10:11:30 [LMAG_SET]:30000                            ← LOW MAGNIFICATION SETTING
2010_06_02_10:12:10 [AF_INI]:20000                              ← AUTOMATIC FOCUSING START POINT
2010_06_02_10:12:15 [AF_FIN]:25000                              ← AUTOMATIC FOCUSING END POINT
2010_06_02_10:12:18 [DEF_RECOG]:0010,150001500,150002500        ← DEFECT #1 DETECTION RESULT
2010_06_02_10:12:20 [HMAG_SET]:100000                           ← DEFECT IMAGING MAGNIFICATION SETTING
2010_06_02_10:12:21 [IMG_GET]                                   ← IMAGING EXECUTION
                         .
                         .
                         .
2010_06_02_10:13:00 [ADR_END]                                   ← ADR END
2010_06_02_10:13:01 [RECIPE_END]                                ← RECIPE EXECUTION END
2010_06_02_10:12:02 [WF_UNLOAD]                                 ← SAMPLE WITHDRAWAL
```

FIG.13

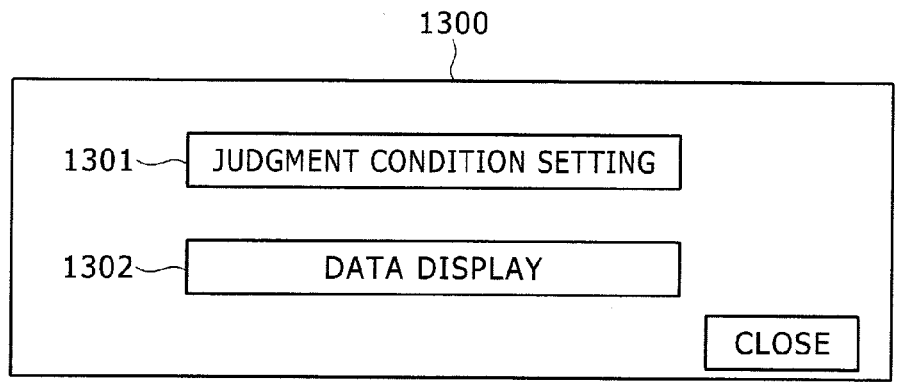

- 1401: TYPE NAME — xxxxxxx ▼
- 1402: PROCESS NAME — xxxxxxx ▼
- 1403: LOT ID — NOT SPECIFIED ▼
- 1404: WAFER ID — NOT SPECIFIED ▼

1405 — MONITORING ITEM

| No. | xxxx | xxxxxxxxxxxxxxxxxxxxxxxxxxxx ▼ |

1406 — JUDGMENT DATA

- ☐ LATEST DATA
- ☑ MOVING AVERAGE  xx  pcs

1407 — JUDGMENT REFERENCE VALUE

- ☐ ARBITRARY   UCL [ ]   LCL [ ]
- ☑ STANDARD DEVIATION   DATA PARAMETER  xx  pcs   UCL/LCL AVERAGE±  x  σ

1408 — ALERT MESSAGE

| Code | xxxx | xxxxxxxxxxxxxxxxxxxxxxxxxxxxxxxxx |

1409 — [REGISTER] [CANCEL] [RETURN] [CLOSE]

FIG. 17

| MONITORING ITEM No. | DATE/TIME | TYPE NAME | PROCESS NAME | LOT ID | WAFER ID | DATA No. | DATA | UCL | LCL | JUDGMENT RESULT |
|---|---|---|---|---|---|---|---|---|---|---|
| xxxx | xxxx/xx/xx | xxxxxxx | xxxxxxxx | xxxxxxx | xx | xxxx | xxxx | xxxx | xxxx | xxxx |

OUTPUT   GRAPH DISPLAY   SEARCH SCREEN   CLOSE

FIG.18

| DATE/TIME | No. | Code | ALERT MESSAGE |
|---|---|---|---|
| xxxx/xx/xx | xxxx | xxxx | xxxxxxx |
| xxxx/xx/xx | xxxx | xxxx | xxxxxxx |
| xxxx/xx/xx | xxxx | xxxx | xxxxxxx |
| xxxx/xx/xx | xxxx | xxxx | xxxxxxx |
| xxxx/xx/xx | xxxx | xxxx | xxxxxxx |
| xxxx/xx/xx | xxxx | xxxx | xxxxxxx |
| xxxx/xx/xx | xxxx | xxxx | xxxxxxx |

OUTPUT | GRAPH DISPLAY | SEARCH SCREEN | CLOSE

001
CHARGED PARTICLE BEAM DEVICE, DEFECT OBSERVATION DEVICE, AND MANAGEMENT SERVER

TECHNICAL FIELD

The present invention relates to a charged particle beam device and a defect observation device which are used for inspection, observation, measurement, etc. of samples and a management server which is connected to such devices via a network.

BACKGROUND ART

Semiconductor wafers, glass substrates, etc. are used for manufacturing semiconductor chips, photo masks, magnetic disks, liquid crystal displays, and so forth. In the manufacturing processes of such products, fluctuation of the manufacturing process or a foreign object or pattern appearance inferiority (hereinafter referred to as a "defect") on the surface of a semiconductor wafer, glass substrate, etc. can lead to defectives and inferior products. For this reason, the semiconductor wafers and glass substrates are inspected in some way in the middle of the manufacture and the occurrence of abnormalities is monitored during the manufacturing process. When some type of abnormality is found, the cause of the occurrence of the abnormality is determined immediately, the manufacturing conditions are adjusted or changed, and countermeasures are taken so as to prevent the occurrence of the same type of defects to the products manufactured.

The detection of abnormalities is carried out by methods like defect/abnormality detection by use of an external appearance inspection device, pattern dimension fluctuation monitoring by use of a length measurement device (CD-SEM), defect monitoring by fixed point observation by use of a defect review device, etc. The CD-SEM is a device for measuring the dimensions of lines, spaces, contact holes, etc. in a circuit pattern. The CD-SEM performs the fixed point observation in regard to the dimensions of multiple parts of the sample and detects a process abnormality by using fluctuations in the length measurement values. The external appearance inspection device is a device for acquiring images of the sample and calculating defect positions by comparative calculation with an appropriate reference image or an adjacent circuit pattern. There are some types of external appearance inspection devices, such as bright field external appearance inspection devices, dark field external appearance inspection devices and scanning electron microscope (SEM) external appearance inspection devices. The defect review device is a device for capturing images of preset review positions and thereby judging whether a defect exists in the acquired images or not or analyzing the types of defects existing in the acquired images. Through the analysis of the types of the defects occurring at the positions of the fixed point observation and composition analysis of the defects, the above devices can be used as process monitoring tools for automatically detecting abnormalities or fluctuations occurring in the manufacturing process.

When the aforementioned CD-SEM, external appearance inspection device or defect review device is used as a process monitoring tool, measurement/inspection in the same conditions are performed on the same type of wafers by using software called a "recipe" describing conditions of the measurement/inspection. When an abnormal measurement/inspection result outside the supposition by the recipe is detected due to fluctuation in the process conditions, the device judges that some type of error has occurred and stops the operation. Therefore, the recipe has to be changed or readjusted each time when the process conditions are changed.

Patent Literature 1 has disclosed a recipe diagnosis device which is configured to allow the recipe setter (who sets the recipe) to grasp the timing of execution of the recipe adjustment, by comparing a scanning electron microscope's operating conditions (which have been set based on the recipe) with history information on the operating conditions and displaying the temporal transition of the fluctuating values of the operating conditions on a monitor. According to the invention described in the literature, the recipe setter is enabled to make the recipe adjustment with appropriate timing, and consequently, to maintain the automation rate of the scanning electron microscope at a high level.

Patent Literature 2 has disclosed an invention for increasing the accuracy of management of log data of a substrate processing device such as an optical exposure device and an EUV device. The invention increases the management accuracy of the log data (such as information representing the transition of the substrate processing, information regarding the contents of the substrate processing which has been executed, and measurement information representing the results of various types of measurement performed during the substrate processing) by recording the log data together with identification information representing a component of the substrate processing device.

PRIOR ART LITERATURE

Patent Literature

Patent Literature 1: JP-2010-87070-A
Patent Literature 2: JP-2006-128447-A

SUMMARY OF THE INVENTION

Problem to be Solved by the Invention

The process monitoring tool is a device for monitoring the occurrence of abnormalities in a manufacturing process as mentioned above. If the performance of such a process monitoring tool is deteriorated by some factor, errors like overlooking of product abnormality can occur, leading to fatal trouble to the process. Therefore, stable operation is required of such devices.

Thus, the devices used as process monitoring tools are essentially required to have the function of detecting a device abnormality or a sign of occurrence of an abnormality and giving a feedback to the inspection/measurement (i.e., interrupting and reexecuting the inspection/measurement).

The invention described in the Patent Literature 1 judges the appropriateness of the already-set recipe setting values by using status information on the measurement device or the wafers that was acquired at the time of the recipe setting. Therefore, abnormality detection in case of an unexpected device performance deterioration occurring in the middle of the execution of the measurement/inspection is impossible.

It is therefore the primary object of the present invention to provide a device capable of quickly detecting an abnormality by which the reliability of the device is deteriorated or a sign of occurrence of such an abnormality.

Means for Solving the Problem

In the present invention, a monitoring item for monitoring the operating status of the device is set appropriately, and fluctuation of the monitoring item with respect to history information on the monitoring item is calculated by comparing the value of the monitoring item which was set at the time of the execution of the inspection/measurement sequence with the history information on the monitoring item. The calculated fluctuation is outputted in a format understandable to the operator of the device and provided as information useful for judging the presence/absence of occurrence of an abnormality.

Effect of the Invention

According to the present invention, an abnormality resulting from deterioration in the device performance reliability can be detected early enough, by which an increase in the process trouble due to deterioration in the reviewing performance can be prevented.

BRIEF DESCRIPTION OF THE DRAWINGS

FIG. 6 is a table showing an example of monitoring items in accordance with the present invention.

FIG. 12 is a schematic diagram for explaining a storage format of history information.

FIG. 13 is a schematic diagram showing an example of a screen for setting monitoring judgment criteria in accordance with the present invention.

FIG. 14 is a schematic diagram showing an example of a screen for selecting displayed data in accordance with the present invention.

FIG. 17 is a schematic diagram showing an example of a screen for list display of a data list in accordance with the present invention.

FIG. 18 is a schematic diagram showing an example of a screen for displaying an alert in accordance with the present invention.

MODE FOR CARRYING OUT THE INVENTION

Figure 1:
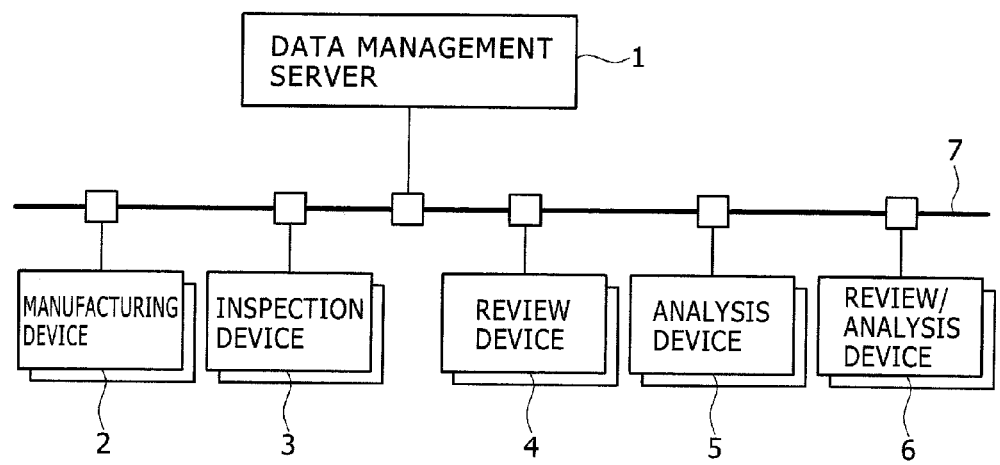
FIG. 1 is a block diagram showing an example of a semiconductor wafer manufacturing line.

In the following, a preferred embodiment in accordance with the present invention will be described in detail by properly referring to figures, wherein each element common to multiple figures are assigned the same reference character and repeated explanation thereof is omitted for brevity.

First, a concrete example of the connection configuration of devices arranged in a manufacturing line of semiconductor wafers will be explained below referring to FIG. 1. The semiconductor wafer manufacturing line includes a data management server 1, a semiconductor wafer manufacturing device 2, an inspection device 3, a review device 4, an analysis device 5, and a review/analysis device 6. These devices are connected together by a network 7.

The data management server 1 manages data which are acquired by the inspection device 3, the review device 4, the analysis device 5 and the review/analysis device 6.

The manufacturing device 2 includes some types of devices used for manufacturing the semiconductor wafers, such as an exposure device, an etching device and a deposition device. The inspection device 3 inspects the semiconductor wafers and detects defect positions, defect sizes, etc. For example, the inspection device 3 scans an optical beam spot on the semiconductor wafer and determines the defect positions based on the diffuse reflection intensity of the scanned optical beam spot. The inspection device 3 may also perform the detection of the defect positions by recognizing the inspection image's parts differing from a reference image as the defects. The methods for detecting defects are already-known techniques and thus detailed explanation thereof is omitted here. The inspection device 3 sends coordinate data of the defect positions to the review device 4, the analysis device 5 and the review/analysis device 6 via the data management server 1 or directly.

The review device 4 displays and observes the defects based on the defect positions acquired by the inspection device 3. For example, the defect observation is carried out by properly positioning each targeted defect (under consideration) existing on the semiconductor wafer based on the defect position coordinate data by moving a stage on which the semiconductor wafer has been set.

The review device 4 may be implemented by a SEM, an optical microscope using visible light, a microscope using ultraviolet light, etc. Any type of device having the function of magnifying and capturing images of the object can be employed for the review device 4 irrespective of the type and intensity of the energy used and the method of visualizing the object. The analysis device 5 performs the elemental analysis based on the coordinate data of the defect positions by employing EDX and/or Auger electron spectroscopy, for example. The Auger electron spectroscopy is a well-known elemental analysis method detecting Auger electrons which are emitted from the object in response to the irradiation of the object with the electron beam. The review/analysis device 6 performs the defect observation and the elemental analysis based on the coordinate data of the defect positions.

Incidentally, these devices for the inspection, observation and analysis do not necessarily have to be provided as separate devices. Combining some devices together (so as to perform both the inspection and the review (observation) in one device, for example) is also possible. While an example of a semiconductor wafer manufacturing line is illustrated here, any type of connection configuration may be employed as long as the use of data among devices is possible.

The samples flowing on the semiconductor manufacturing line are managed in units called "lots", each including a prescribed number of (ten-odd) wafers. The wafer processing conditions in each device are also set in units of lots (for each lot) in many cases. In the case of process monitoring, the process can be performed in units of wafers (for each wafer) or in units of some wafers depending on the case. In the following explanation, a wafer or a group of wafers (one lot, one wafer, one set of wafers as a unit, etc.) that is automatically processed from the input (conveyance) to the output of each device will be referred to as a "set".

Since the samples flow through the devices process by process as shown in FIG. 1 in a semiconductor wafer manufacturing line or the like, an abnormality occurring in a device has to be detected early enough, otherwise the samples processed abnormally flow to the next process. Since the percentage of defectives and the cost for the reprocessing increase with the increase in the number of the abnormally processed samples flowing to the next process, it is critically important to detect each abnormality early at the stage of the occurrence.

Therefore, in this embodiment, in some steps in the processing flow of a set of samples (that is, in some steps between the carrying in and the carrying out of the set of samples to/from the device), values of monitoring items actually set or calculated are monitored according to a previously generated recipe (monitoring) and the actual values of the monitoring items are displayed on a display unit while comparing them with corresponding history information of the past.

Here, the "monitoring items" mean items that have previously been set in order to evaluate the operation of imaging means and/or that enable evaluation of performance of the device. For example, the monitoring items may include setting values that have been set to an electronic optical system, adjustment values that are used for the positioning of the beam irradiation position, processing results that indicate the device's processing performance for one sample included in the set of samples, etc.

This embodiment can be employed for each device shown in FIG. 1. Specifically, results of the operation of each sample-processing device (manufacturing device 2, inspection device 3, review device 4, analysis device 5, review/analysis device 6, etc.) are stored as history information in each device, in the data management server 1, or in an external storage device (not shown) connected via a network, and the values of the monitoring items when each new sample is processed and the corresponding history information in the past are displayed in a comparative format. Especially when the monitoring items are evaluated remotely, that is, evaluated by a remote operation device (a device other than the device performing the operation as the monitoring target) such as the data management server, the history information may either be transmitted from each device in response to a request from the remote operation device. A storage device for accumulating the history information on all the devices may also be provided on a network. The history information may also be accumulated in a storage device included in the remote operation device.

In this case, the display unit may either be provided on each device, on the data management server 1, or on an external terminal connected via a network. The displaying on an external terminal allows the manager, etc. to recognize abnormalities early at a position remote from the manufacturing line.

This embodiment makes it possible to detect the abnormalities in real time. Further, the displaying of the monitoring items in comparison with the past history information allows the operator, manager, etc. to recognize abnormality with ease and to immediately give a feedback to the sample that was the target of processing at the time of occurrence of the abnormality.

Preferably, when the value of a monitoring item in a new process (being compared with the past history information) exceeds a preset reference width, the device is judged to be in an abnormal state and a warning is issued to the operator or the process is interrupted. Since this configuration allows the operator, manager, etc. to clearly recognize the occurrence of the abnormality, countermeasures against the abnormality can be started immediately and ill effects of the device abnormality can be lessened.

It is more preferable if the reference width used for the judgment, the past history information used for the comparison, or the method of the judgment can be set through a GUI (Graphical User Interface). This configuration allows the manager, etc. to desirably set the criteria for the judgment on each abnormality, and thus flexible operation becomes possible for each device, each process and each sample type.

In the following, an example regarding the review device will be described as a first example and an example regarding a charged particle beam device in general will be described as a second example. An example of a GUI used in the first and second examples will be illustrated as a third example.

FIRST EXAMPLE

In this example, an example of application to a defect review device will be described.

Figure 2:
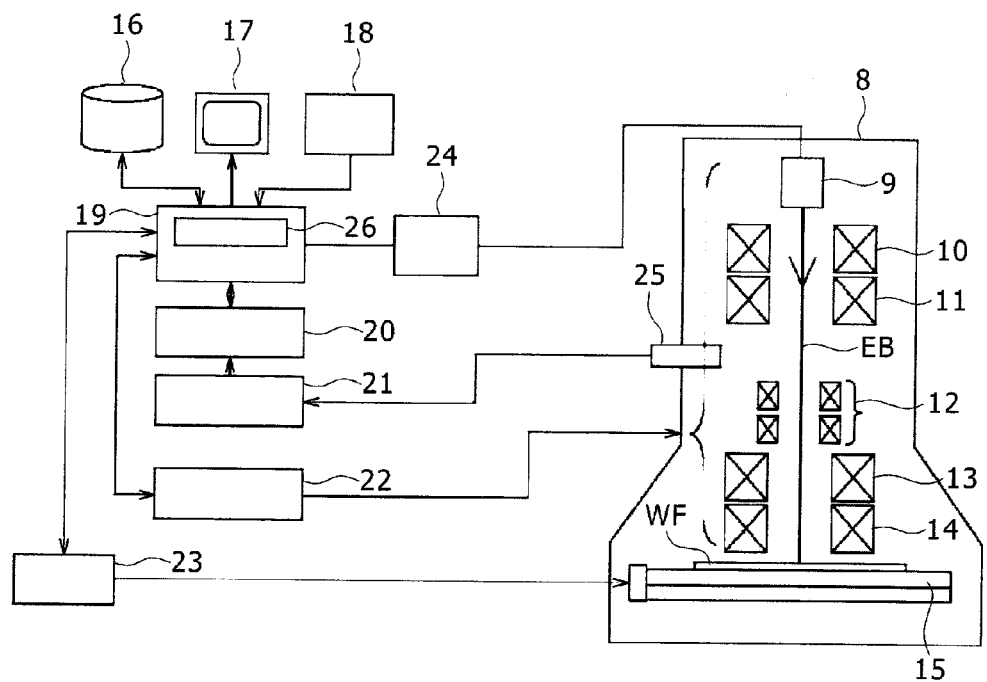
FIG. 2 is a schematic block diagram showing the configuration of a review device.

A review device 4 employing a SEM will be described below referring to FIG. 2. The review device 4 receives defect position information transmitted from an external appearance inspection device detecting the defects. Further, a set of samples which has been inspected by the external appearance inspection device is conveyed to the review device 4. The review device has sample storage means (not shown) for storing a set of samples conveyed thereto. A sample to be observed is selected successively from the set of samples, moved to a sample room via the review device's sample preparation room (not shown), and set on a sample stage 15.

The review device 4 in this example is equipped with an imaging device 8. The imaging device 8 includes an electron source 9, an electronic optical system which will be explained below, the stage 15, and a detector 25. These components constitute a SEM.

The electronic optical system for irradiating the sample with an electron beam EB includes condenser lenses 10 and 11, a deflection scanning coil 12, and objective lenses 13 and 14. The electron beam EB emitted from the electron source 9 is converged by the condenser lenses 10 and 11 and deflected by the deflection scanning coil 12 to scan the sample. The electron beam EB is further converged by the objective lenses 13 and 14 and focused on the sample WF on the stage 15 so as to irradiate and scan the sample WF. In response to the irradiation, secondary charged particles (secondary electrons, reflected electrons, etc.) having information on the sample are emitted from the sample WF and detected by the detector 25. The output from the detector 25 is digitized by an A/D converter 21 and an image is generated by an image calculation unit 20 by associating the scanning positions of the electron beam with pixels. Further, image processing, such as defect extraction by calculating a differential image between the image of the inspection target and a reference image (image of a normal part corresponding to the defect position), is carried out as needed. The output from the image calculation unit 20 is sent to a monitor 17 via a control unit 19 which controls the entire device, by which a SEM image of the sample WF is displayed on the monitor 17.

The user inputs parameters in regard to input items (defect observation conditions, operation result monitoring conditions, etc.) through an input device 18 (mouse, controller, console, etc.). The inputted parameters are sent to the control unit 19. The control unit 19 sends control signals to an electronic optical system control unit 22 (controlling the lenses and coils forming the electronic optical system) and a high-voltage stabilized power supply 24 and sets imaging conditions of the SEM. The components of the electronic optical system operate according to the imaging conditions. The defect coordinate data outputted from the inspection device 3 is sent to the control unit 19 via an unshown network, and observation positions are determined based on the defect coordinate data. The control unit 19 controls a stage control unit 23 according to the determined observation positions. The stage 15 is moved in X and Y directions under control of the stage control unit 23.

The review device 4 further includes a storage device 16 such as a hart disk drive and stores the acquired SEM images and the history information (e.g., information on the operating status of the device at the points of acquisition of the SEM images) in the storage device 16.

The control unit 19 includes a data analysis calculation unit 26 which executes the monitoring and storing of the device status, the comparison with the past operation results, and the judgment on whether the standards are satisfied or not. The data analysis calculation unit 26 may also be provided separately from the review device 4 (e.g., as a function of the data management server 1). It is also possible to further provide a separate special-purpose data analysis calculation device. The data analysis calculation unit 26 may either be implemented as hardware or installed as software in the control unit 19 inside the review device or in a processing device provided outside the review device.

An example of the flow of a review processing sequence proposed by the present invention will be explained below referring to FIG. 3. In the first step 301, the defect coordinate data is acquired from the inspection device 3. In the next step 302, a wafer to be observed is selected from a set of wafers conveyed to the review device 4 and the selected wafer is inserted into the sample room. In step 303, the electronic optical system control unit 22 sets electric current values and voltage values for controlling the lenses and electrodes of the electronic optical system based on information regarding electron beam control status which has previously been set in the recipe. In the next step 304, wafer alignment for the positioning of the wafer is started. The stage is moved to alignment coordinates in step 305 and the coordinates of the alignment point are detected in step 306. Then, the amounts of offset and rotation are calculated in step 307 by the data analysis calculation unit 26 via the control unit 19 from the distance between the visual field center as the result of the stage movement (stage absolute coordinates) and the coordinates detected as the alignment point, by which the coordinate origins of the sample and the device are associated with each other.

In the next step 308, fine alignment for compensating for the defect coordinate errors is started. The stage is moved to a set of defect coordinates in step 309 and defect coordinates are detected in step 310. Then, the amounts of offset and rotation are calculated in step 311 by the data analysis calculation unit 26 via the control unit 19 from the distance between the coordinates of the visual field center as the result of the stage movement and the detected defect coordinates, by which the defect coordinates and the stage coordinates are adjusted with high precision.

In the next step 312, ADR is started. The ADR stands for automatic defect reviewing, in which a plurality of defect positions existing on the sample are observed automatically based on previously acquired defect position information. Subsequently, the stage is moved to a set of defect coordinates in step 313, a low-magnification image is acquired in step 314, and whether a defect has been detected or not is judged by means of image processing in step 315. If no defect has been detected, a procedure of moving the stage to the next set of defect coordinates and acquiring a low-magnification image is repeated until a defect is detected. When a defect is detected, the amount of offset is calculated in step 316 by the data analysis calculation unit 26 via the control unit 19 from the distance between the coordinates of the visual field center as the result of the stage movement and the detected defect coordinates. Subsequently, the defect is centered (centering), that is, moved to the visual field center in step 317 and automatic focusing is conducted in step 318 at a magnification ratio suitable for detailed observation of the defect. In this case, the objective lens is controlled in step 319 by the data analysis calculation unit 26 via the control unit 19 by calculating the change in the electric current applied to the excitation coil of the objective lens. Thereafter, a high-magnification image is acquired in step 320. The steps 313-320 are repeated n times (n=the number of defects).

After observing all the defects, a high-magnification image acquisition ratio is calculated and stored in the storage device 16 in step 321 by the data analysis calculation unit 26 via the control unit 19, by which the ADR is finished. The definition of the high-magnification image acquisition ratio will be explained later.

Further, in step 322, a criterion of judgment previously inputted through the input device 18 and history information on the high-magnification image acquisition ratios in the past are acquired from the storage device. The acquired data are compared in step 323. If the criterion is exceeded, an alert indicating the occurrence of an abnormality is issued on a display unit in step 324. The alert may be issued not only by using the monitor 17 but also by using another system (e.g., the data management server 1) via the network 7, by using a warning lamp, etc. The alert may be issued on two or more such display units.

Depending on the contents of the alert, it is also possible to let the user set the values of the monitoring items again or to allow the device to automatically deal with the abnormality by finely adjusting and setting the values of the monitoring items to appropriate values. However, it is desirable also in this case to record the occurrence of the abnormality and present the record to the user.

In step 325, the wafer is unloaded. The steps from the step 321 (calculation and storage of the high-magnification image acquisition ratio) to the judgment step 323 (comparison with the history information) for the current wafer (surrounded by the dotted lines) will hereinafter be referred to collectively as a "monitoring step 326".

With the flow described above, an abnormality that leads to deterioration in the reviewing performance or a possibility of such an abnormality can be detected early enough, by which the increase in the processing trouble can be prevented.

Incidentally, the monitoring step 326 does not necessarily have to be performed on every execution of the sequence; it is also possible to proceed to the wafer unloading (325) after finishing the step 321. In this case, the ordinary review process is performed, and only when necessary (according to the operator's operation on the GUI), the high-magnification image acquisition ratio calculated and stored in the step 321 is loaded from the storage unit and displayed on the screen while comparing it with the high-magnification image acquisition ratios in the past. However, executing the monitoring step 326 (in which the alert is issued automatically) is advantageous for more clearly informing the operator of the occurrence of an abnormality.

Figure 4:
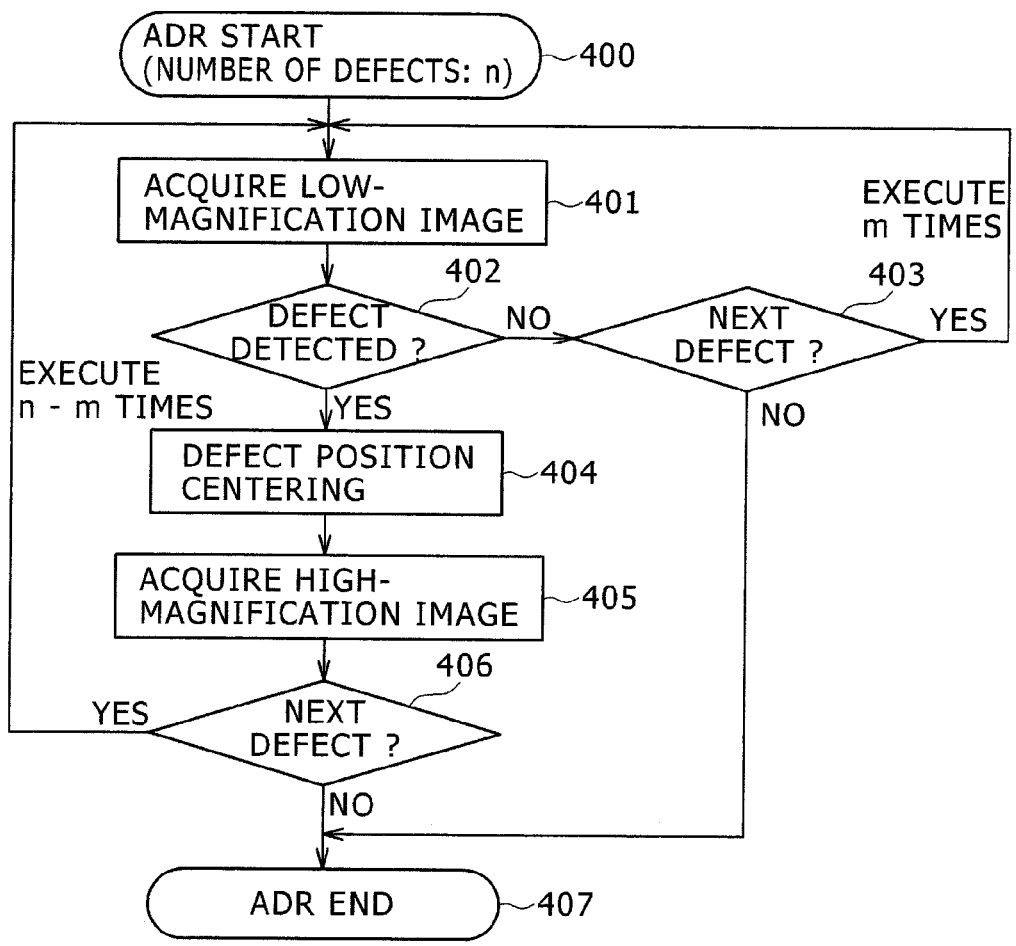
FIG. 4 is a flow chart for explaining the definition of a high-magnification image acquisition ratio in accordance with the present invention.

Next, the definition of the high-magnification image acquisition ratio and the method for calculating the high-magnification image acquisition ratio will be explained below referring to FIG. 4. At the start of the ADR for n defects (400), a low-magnification image is acquired first in step 401 and whether a defect has been detected or not is judged in step 402 by means of image processing. When it is judged that no defect has been detected, the process returns to the step 401 (acquisition of a low-magnification image of the next defect) without acquiring a high-magnification image on condition that there exists the next defect in a judgment step 403. When it is judged in the step 402 that a defect has been detected, the detection position coordinates are moved to the visual field center in step 404 and a high-magnification image is acquired in step 405. Assuming that the number of times of detecting no defect is m, the ADR is finished in step 407 after performing the high-magnification image acquisition step 405 (n−m) times until step 406 judges that there is no next defect. Here, the high-magnification image acquisition ratio is defined as the ratio of the number (n−m) of times of the high-magnification image acquisition to the number n of defects as shown in the following expression:

high-magnification image acquisition ratio (%)= $(n-m)/n \times 100$

This means that the device succeeded in capturing (n−m) observation images.

The data analysis calculation unit 26 monitors this value, stores it in the storage device 16, and compares it with the high-magnification image acquisition ratios in the past. If the value is extremely lower compared to the high-magnification image acquisition ratios in the past stored in the storage device 16, there is a possibility of an abnormality such as the overlooking of defects in the ADR.

The calculated high-magnification image acquisition ratio is displayed on a display unit (e.g., the monitor 17) in a form in which the ratio can be compared with the high-magnification image acquisition ratios in the past. While a GUI that will be illustrated in the third example can be employed, for example, any type of display format may be employed as long as the current processing result can be compared with past processing results.

With the review device in accordance with this example, the operating status of the process monitoring device, that could be evaluated only when the recipe is set or changed (i.e., in units of lots) in the conventional technology, can be grasped at the point of finishing the inspection/measurement of one wafer. Thus, it becomes possible to detect a device abnormality occurring at the point of inspection/measurement of one wafer included in a lot and to give a feedback to the inspection/measurement of the next wafer in the same lot. This makes it possible to reduce the number of samples undergoing the inspection/measurement in the abnormal state (state with an abnormality) to a minimum. Further, the number of samples undergoing the inspection/measurement in the abnormal state and flowing to the next process can be reduced dramatically in comparison with the conventional technology.

SECOND EXAMPLE

While the high-magnification image acquisition ratio was employed in the first example as an item for judging the processing performance of the review device, an example of evaluation of a monitoring item representing the operating status of a charged particle beam device processing samples will be described in the second example.

In this example, not only such an item regarding a device's final output performance (e.g., the high-magnification image acquisition ratio) but also setting items, etc. for controlling the imaging means are handled as the monitoring items. In addition to the monitoring step in the first example, monitoring steps are set in the imaging sequence for one sample.

Since this configuration allows the user to detect a device abnormality even in the middle of a processing flow for one sample, countermeasures against the abnormality can be taken before the sample processed at the time of occurrence of the abnormality proceeds to the next process. Further, setting a plurality of monitoring items helps to clarify in which part of the device or in which processing step the abnormality occurred, by which the determination of the cause of the abnormality is facilitated.

The following explanation of the second example will be given by taking a review device as an example of the charged particle beam device even though the present invention is not restricted to review devices. In the following description, explanation of elements in common with the first example is omitted for brevity.

Figure 3:
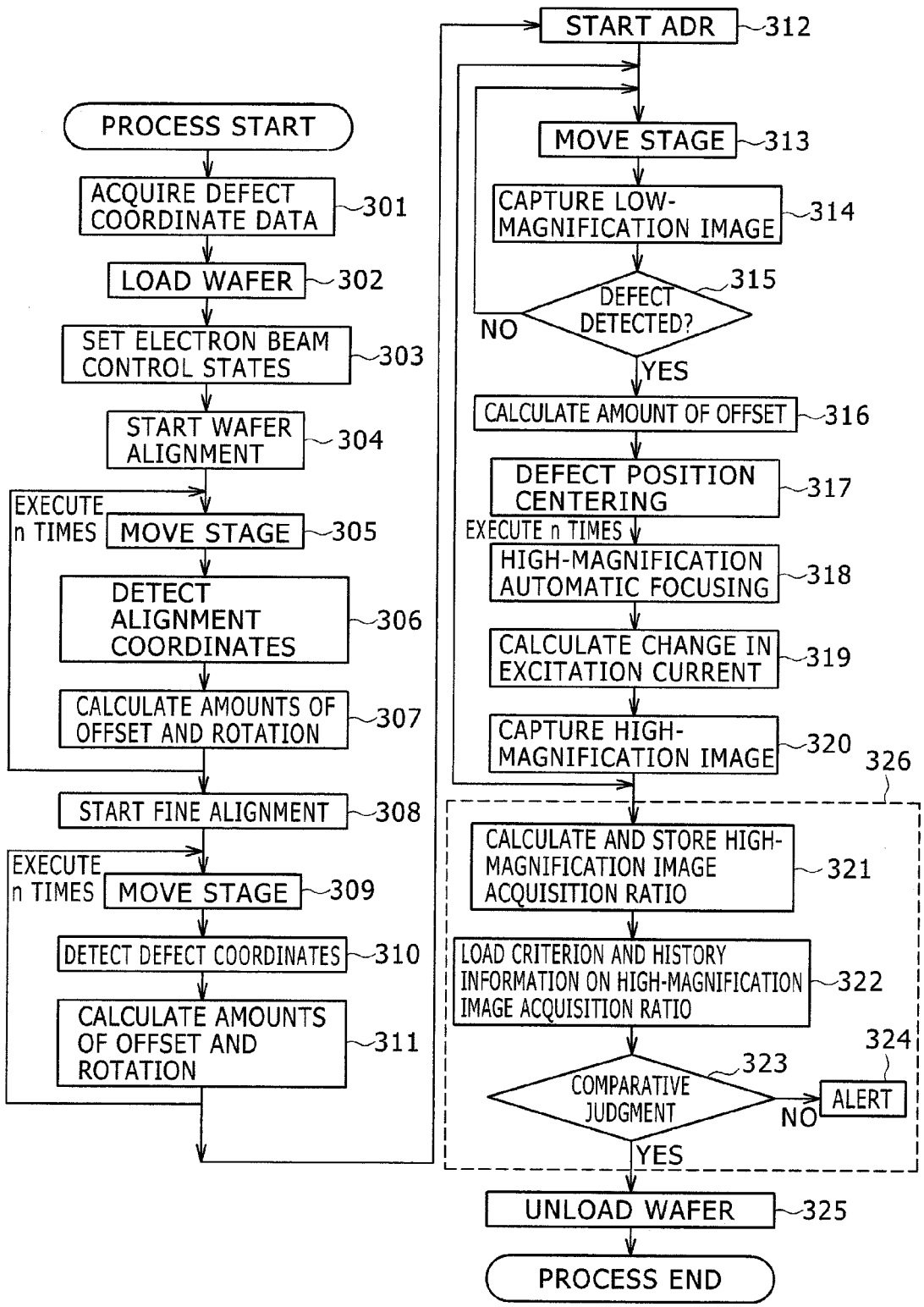
FIG. 3 is a flow chart for explaining the flow of the embodiment in a first example.
Figure 5A:
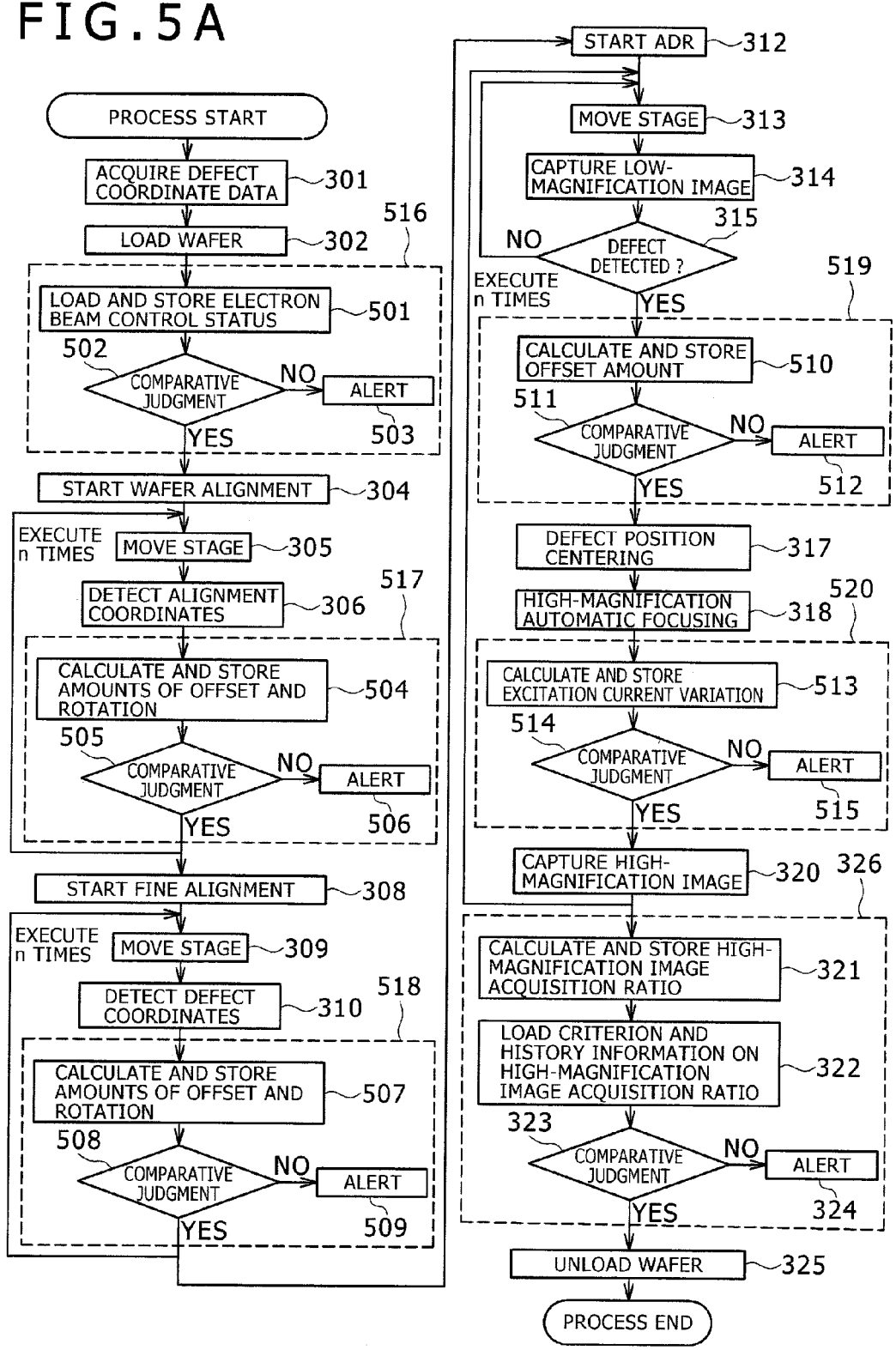
FIG. 5(a) is a flow chart for explaining the flow of the embodiment in a second example.

FIG. 5(a) shows an example in which control parameters for the electronic optical system of the review device, adjustment values used for the adjustment of the beam irradiation position, etc. are also handled as the monitoring items in addition to the monitoring item in FIG. 3. Steps in FIG. 5(a) identical with those in FIG. 3 are assigned the same reference characters and repeated explanation thereof is omitted for brevity.

Step 516 is a monitoring step for monitoring electron beam control status which will be explained in detail referring to FIG. 5(b). Specifically, the electron beam control status may include the filament current, the voltage of a probe current control electrode, the voltage of an extraction electrode, the voltage of an acceleration electrode, voltages applied to other electrodes and coils for controlling the path of the electron beam, etc. The monitoring step 516 includes step 501 of acquiring set values of the current and voltages from the electronic optical system control unit 22 and storing the set values in the storage device 16, step 502 of judging abnormality by comparing the acquired set values with corresponding history information, and step 503 of issuing an alert when it is judged that an abnormality has occurred.

Similar processes are executed in steps 504, 505 and 506 for the amounts of offset and rotation in the wafer alignment (hereinafter referred to as a "monitoring step 517"), in steps 507, 508 and 509 for the amounts of offset and rotation in the fine alignment (hereinafter referred to as a "monitoring step 518"), in steps 510, 511 and 512 for the amounts of offset and rotation in the low-magnification image (hereinafter referred to as a "monitoring step 519"), and in steps 513, 514 and 515 for the excitation current variation (change in the excitation current) of the objective lens (hereinafter referred to as a "monitoring step 520"). The monitoring steps 516, 517 and 518 are steps executed before the execution of the ADR. The monitoring steps 519 and 520 are steps executed during the ADR for each observation position. The monitoring step 326 is a step executed after finishing the ADR of one wafer. Since the monitoring steps 516, 517, 518, 519 and 520 are shown in simplified forms in FIG. 5(a), the details of the monitoring steps 516, 517, 519 and 520 will be explained below referring to FIGS. 5(b), 5(c), 5(d) and 5(e), respectively.

Figure 5B:
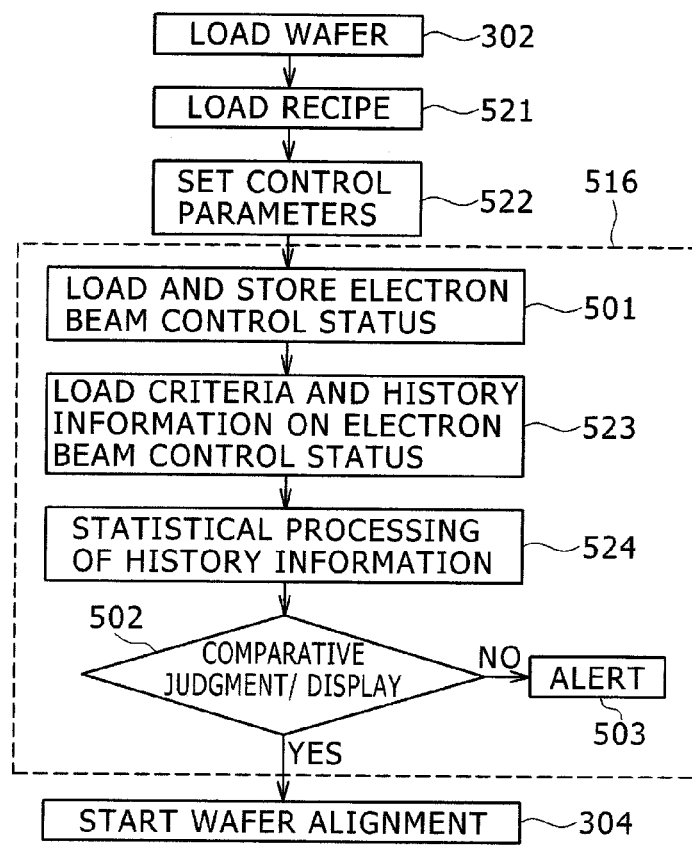
FIG. 5(b) is a flow chart for explaining the flow of the embodiment in the second example.

Referring to FIG. 5(b), the details of the monitoring step 516 for monitoring the electron beam control status will be described.

After the wafer is loaded in the step 302, the recipe as preset observation conditions is loaded. Since the recipe includes the input values for the control parameters of the electronic optical system, values are set to the control parameters of the electronic optical system in step 522 according to the input values. In step 501, the actually set values are loaded and stored in the storage device. The storing in the storage device is preformed in order to retain the set values as history information to be used in the next process. Further, in step 523, history information corresponding to the loaded monitoring items is loaded from the storage device according to conditions such as the number (preset number) of pieces of data to be used for the judgment. Criteria for the judgment are also loaded in this step. In step 524, average values, upper limit values, lower limit values, etc. are determined by statistically processing the loaded history information according to preset criteria. In step 502, the actually set values of the control parameters and the corresponding history information which has been loaded are compared with the values acquired by the statistical processing. The results of the comparison are displayed on a display unit (e.g., the monitor 17) as needed in a format (graph, list, etc.) allowing for the comparison with the past history information. It is also possible to make the display exclusively when necessary in response to an operation by the operator.

When there is a mistake in the setting of the recipe or a failure of the device, one or more values set in the current sequence deviate significantly from the history information. When the criteria are not satisfied, it is judged that an abnormality has occurred and an alert is issued in step 503 to a display unit such as the monitor 17. When the criteria are satisfied, that is, when the currently set control parameters are within reference ranges, the control parameters are judged to have been set normally and the process advances to the next step.

Figure 5C:
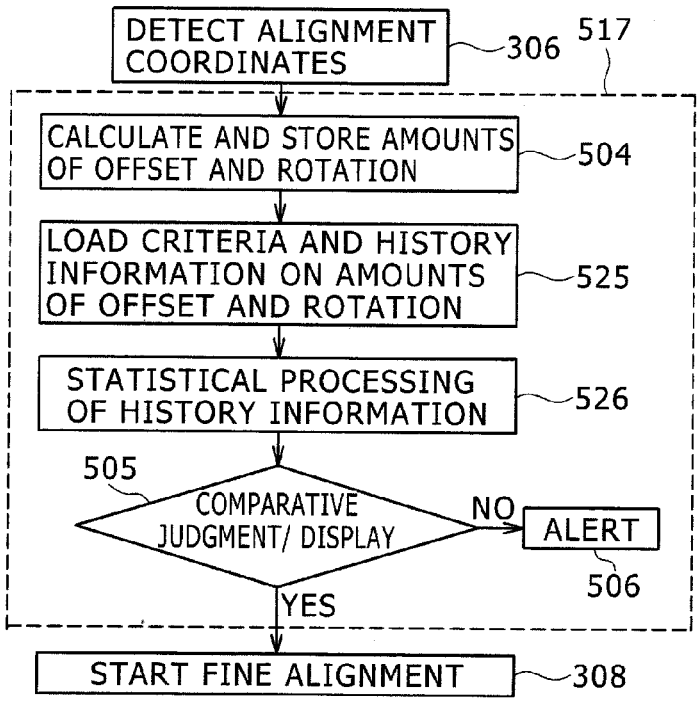
FIG. 5(c) is a flow chart for explaining the flow of the embodiment in the second example.

FIG. 5(c) shows the monitoring step for monitoring the amounts of offset and rotation. Since the monitoring step 517 in the wafer alignment and the monitoring step 518 in the fine alignment do not differ in the process, the following explanation will be given about an example of the wafer alignment as a representative example. In this case, the monitoring item is the amount of offset (offset amount) or the amount of rotation (rotation amount).

After the detection of the alignment coordinates (step 306), based on the difference between the coordinates specific to the device and the coordinates inputted from the inspection device, the amounts of offset and rotation to be used for the conversion of these coordinate systems are calculated by the control unit 19 in step 504. The calculated amounts of offset and rotation are acquired by the data analysis calculation unit 26 and stored in the storage device. In step 525, the history information on the amounts of offset and rotation in the past and the preset criteria are loaded from the storage device. In step 526, average values, upper limit values, lower limit values, etc. are determined by statistically processing the loaded history information according to the criteria. In step 505, the amounts of offset and rotation calculated in the step 504 are compared with the values determined in the step 526 by the statistical processing. When the criteria are not satisfied as the result of the comparison, it is judged that an abnormality has occurred and an alert is issued in step 506. When the criteria are satisfied, it is judged that the setting has been made normally and the process advances to the next step.

Figure 5D:
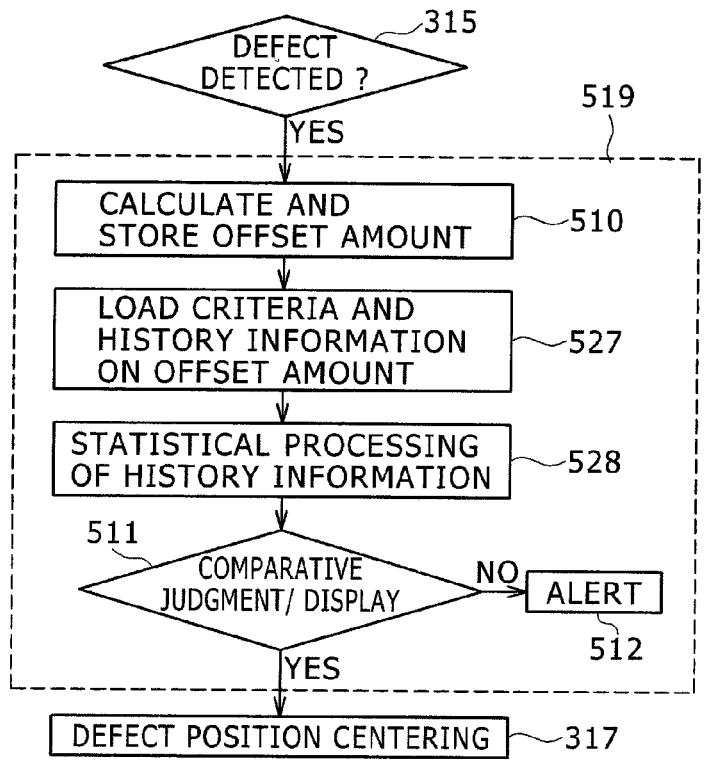
FIG. 5(d) is a flow chart for explaining the flow of the embodiment in the second example.

Referring to FIG. 5(d), the monitoring step 519 in the alignment for adjusting the center of the high-magnification image to the defect position by using the low-magnification image will be explained. In this case, the monitoring item is the offset amount of the defect position with respect to the visual field center. When the detection of a defect is recognized from the low-magnification image in the step 315, the offset amount is calculated based on the detected coordinates and the calculated offset amount is stored in the storage device in step 510. In step 527, the data analysis calculation unit loads the history information on the offset amounts calculated before and the preset criteria from the storage device. In step 528, an average value, an upper limit value, a lower limit value, etc. are determined by statistically processing the loaded history information according to the criteria. In step 511, whether there exists an abnormality or not is judged by comparing the offset amount calculated in the current processing flow with the values acquired by the statistical processing. When the criteria are not satisfied as the result of the comparison, it is judged that an abnormality has occurred and an alert is issued in step 512. When the criteria are satisfied, it is judged that the setting has been made normally and the process advances to the next step.

Figure 5E:
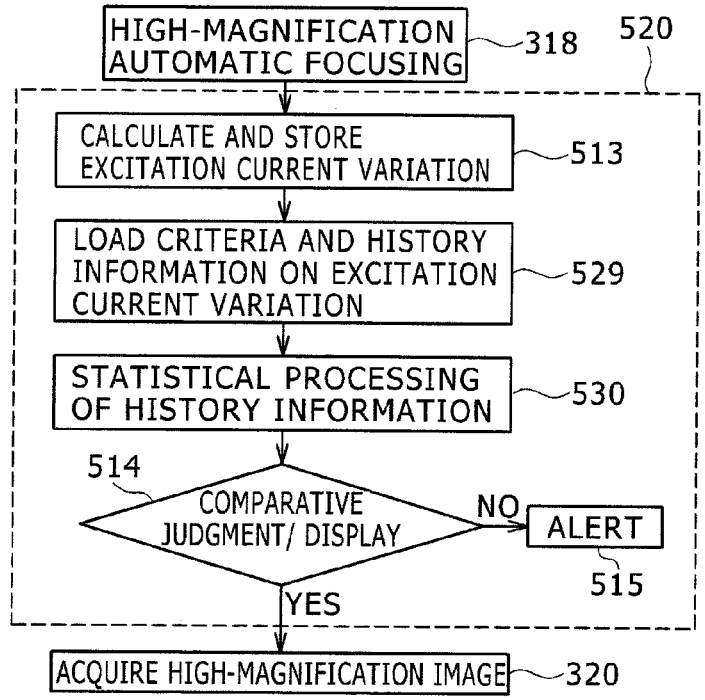
FIG. 5(e) is a flow chart for explaining the flow of the embodiment in the second example.

Referring to FIG. 5(e), the monitoring step 520 for monitoring the excitation current variation (the change in the excitation current) of the objective lens in the automatic focusing will be explained. In this case, the monitoring item is the excitation current variation. In step 318, the automatic focusing is performed by changing the excitation current supplied to the coil of the objective lens. After completing the automatic focusing, the excitation current variation as the difference between the electric current supplied to the coil to set the objective lens at the focused position and an initial electric current (or a prescribed reference electric current) is calculated and stored in the storage device in step 513. In the next step 529, the history information on the excitation current and the preset criteria are loaded from the storage device. In step 530, an average value, an upper limit value, a lower limit value, etc. are determined by statistically processing the loaded history information according to the criteria. In step 514, whether there exists an abnormality or not is judged by comparing the excitation current variation calculated in the current processing flow with the values acquired by the statistical processing. When the criteria are not satisfied as the result of the comparison, it is judged that an abnormality has occurred and an alert is issued in step 515. When the criteria are satisfied, it is judged that the setting has been made normally and the process advances to the next step.

By properly making the judgment on the result of the operation in the middle of the processing flow executed for a set of samples as described above, an abnormality occurring to a part of the device can be detected immediately and countermeasures against the abnormality can be taken without waiting until the end of the process.

Next, the items for judging the processing performance of the device (i.e., the monitoring items) will be explained below referring to FIG. 6. The monitoring of the operating status of the review device 4 is performed at the time of each processing step 61 (monitoring steps 516-520 and 326 shown in FIG. 5(a)) according to the monitoring contents 62. The monitoring items 63 are for the purpose of detecting abnormalities that lead to ADR errors shown in the column "detectable abnormality 64". The details of the monitoring items 63 will be explained later.

The monitoring items shown in FIG. 6 are just an example of basic items. The monitoring items may include any item that enables measurement of a factor affecting the performance of the device, such as the amount of correction of the electron beam deflection, the amount of astigmatism, and the value of the probe current. It is also possible to allow the operator to previously set or select the monitoring items.

Figure 7:
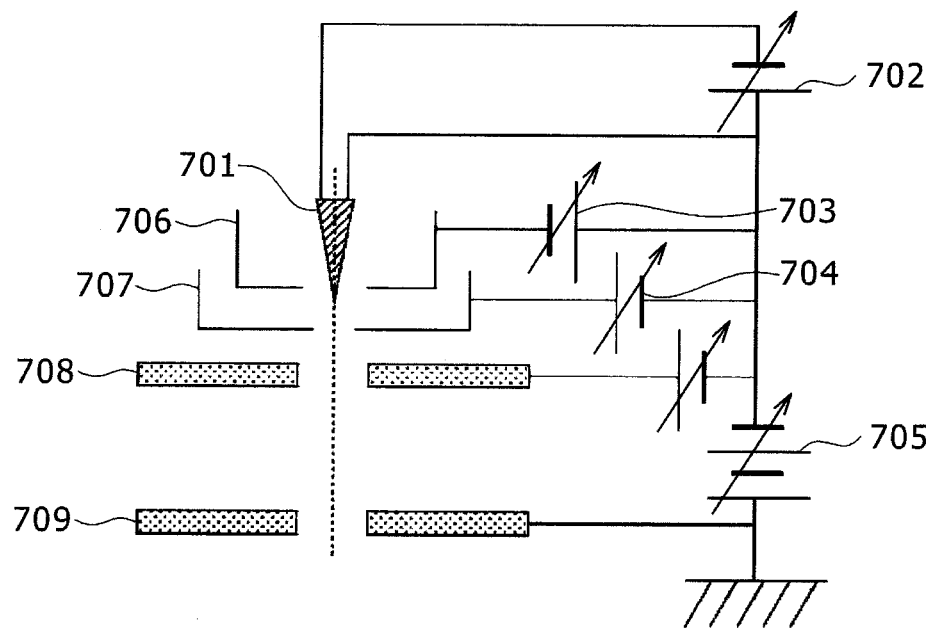
FIG. 7 is a schematic diagram showing items used for monitoring electron beam control status.

Next, the monitoring items related to the electron beam control status will be explained below referring to FIG. 7. FIG. 7 shows the configuration inside the electron gun. In this case, the possibility of image quality deterioration or hardware abnormality can be detected by monitoring the values of filament current 702 for controlling the tip end temperature of a chip 701 emitting the electrons, voltage 703 applied to a probe current control electrode 706, voltage 703 applied to an extraction electrode 707 for controlling the probe current range, and acceleration voltage 703 applied between a control electrode 708 and an acceleration electrode 709.

Figure 8:
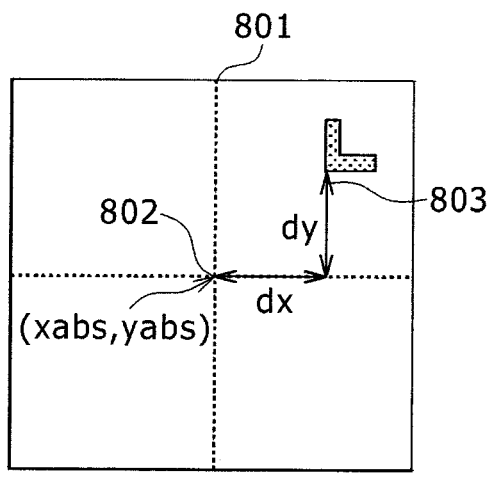
FIG. 8 is a schematic diagram for explaining the definition of an offset amount of wafer alignment.

Next, the offset amount of the wafer alignment will be explained below referring to FIG. 8. When the stage has been moved to the wafer alignment coordinates, the distance (dx, dy) from the center coordinates 802 (xabs, yabs) of the visual field 801 to the reference point 803 of the alignment mark is defined as the offset amount of the wafer alignment and this value is monitored. When the device is operating normally, the offset amount remains stable if the product type and the process do not change. Thus, if the offset amount during the process differs significantly from the offset amounts stored before, there is a possibility of an abnormality such as misrecognition of the alignment coordinates.

Figure 9:
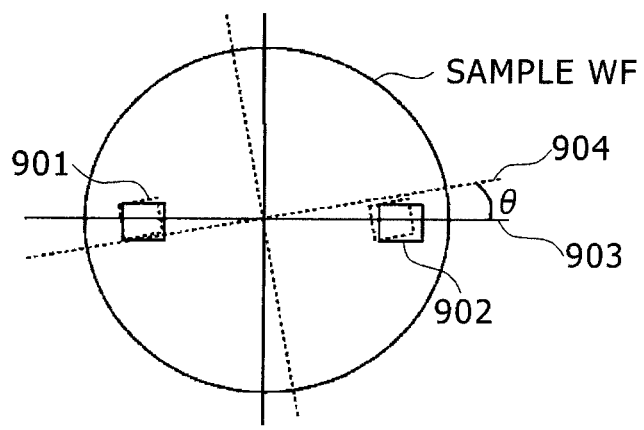
FIG. 9 is a schematic diagram for explaining the definition of a rotation amount of the wafer alignment.

Next, the rotation amount of the wafer alignment will be explained below referring to FIG. 9. The XY axes 904 are recognized by detecting the coordinates of two points 901 and 902 of the alignment pattern. A rotation angle θ calculated from the XY axes 904 recognized in the alignment with respect to ideal stage XY axes 903 is defined as the rotation amount and this value is monitored. When the sample has been set on the stage normally and the same alignment mark as that for a sample processed before is recognized, the rotation amount does not differ much from the past history records. If this rotation amount changes, there is a possibility of an abnormality such as misrecognition of the alignment pattern and inappropriate setting of the wafer on the stage.

Figure 10:
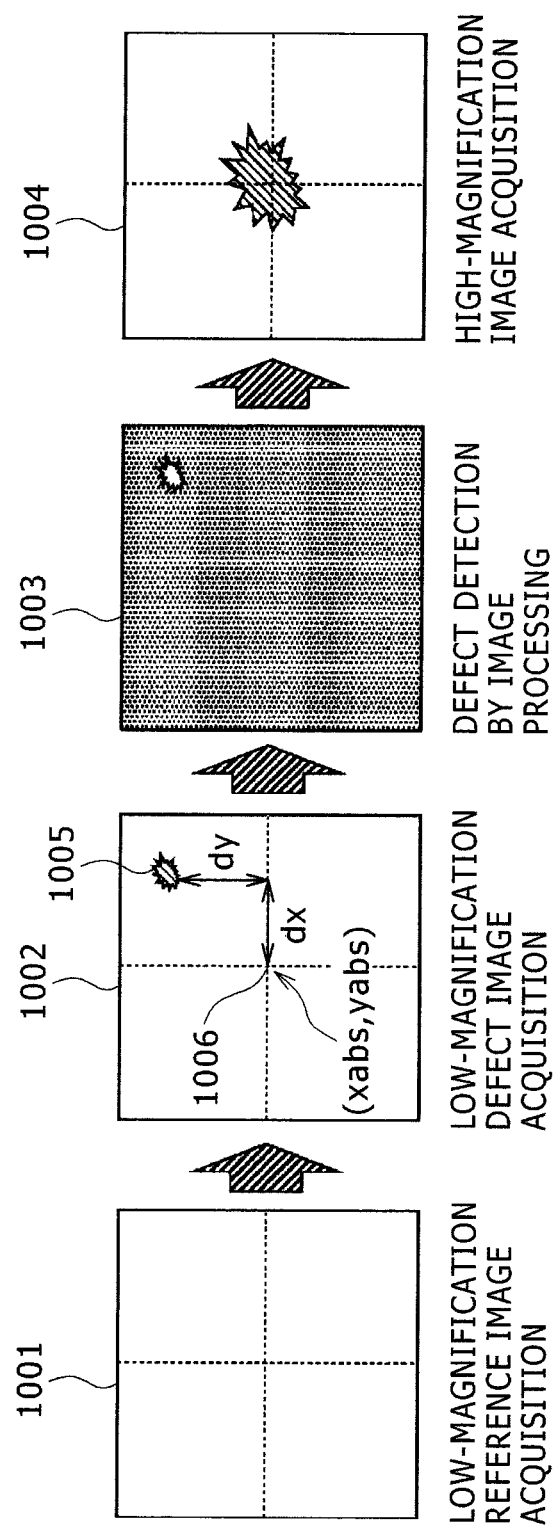
FIG. 10 is a schematic diagram for explaining fine alignment and a defect coordinate error in ADR.

Next, the offset amount of the defect coordinates in the fine alignment and the ADR (low-magnification image acquisition) will be explained below referring to FIG. 10. A high-magnification image 1004 is acquired by detecting a defect by use of a reference image 1001 captured at a low magnification and an image processing result 1003 obtained from a defect image 1002. In this case, the distance (dx, dy) from the visual field center coordinates 1006 (xabs, yabs) of the low-magnification defect image 1002 to the defect detection coordinates 1005 is defined as the offset amount of the defect coordinates and this value is monitored. If this offset amount has significantly changed from the offset amounts in the past, there is a possibility that an abnormality such as misdetection of the defect coordinates has occurred.

Figure 11:
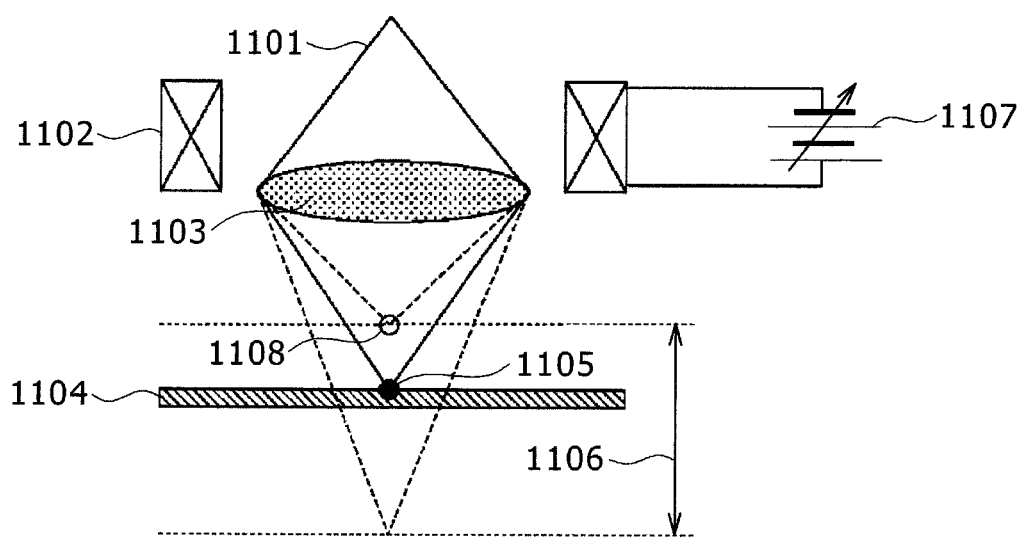
FIG. 11 is a schematic diagram for explaining an excitation current variation of an objective lens.

Next, the excitation current variation (the change in the excitation current) of the objective lens will be explained below referring to FIG. 11. In the SEM, the electron beam 1101 is converged by generating a magnetic field 1103 by feeding electric current through the excitation coil 1102 of the objective lens. The focal point (convergence point) 1105 where the electron beam is most converged can be moved within a control range 1106 according to the electric current 1107 fed through the excitation coil 1102. Therefore, the automatic focusing is carried out by adjusting the electric current 1107 of the excitation coil 1102 so that the focal point 1105 is situated on the surface of the wafer 1104. In this case, the change in the electric current 1107 of the excitation coil 1102 corresponding to the electron beam focal point 1105 (i.e., the difference between the electric current before the control and the electric current after the control (at the focused position)) is monitored. For example, in a case where the focal point situated at the position 1108 before the control (electric current=I) is adjusted to the position 1105 on the surface of the sample by varying the electric current to I', the value acquired by the monitoring equals I'−I. When the device is in the normal state, the variation does not differ much from the variations in the past since the sample height does not change much. If this variation has significantly changed from the variations in the past, there is a possibility that an abnormality such as image blurring (due to inappropriate detection of the focused position) has occurred.

Incidentally, it is also possible to monitor the electric current (fed to the excitation coil) itself, instead of the variation in the electric current.

By monitoring the variation in the electric current fed to the excitation coil as above, the electric current variation at each position (focal point search position) in the focal point control range 1106 becomes clear. This makes it possible to acquire information on the status (deformation, electrification) of the sample from the distribution of the electric current variations on the sample surface.

While an example of the monitoring items has been explained above, other monitoring items (values) may also be employed as long as the values affect the performance of the device and the values can be monitored in the middle of the processing of a set of samples.

Referring to FIG. 12, the contents of a file storing the history information on the above monitoring items will be explained below. As shown in FIG. 12, the history information stored in the storage device includes log data output date/time 1201, a log identification command 1202 and input/output data 1203 (that was set or inputted/outputted), which are associated with each other. Since the history information is automatically appended successively on each operation of the device, the log data are stored in the storage device while being arranged in the order of device operation, that is, in the order of the log data output date/time. The log identification command 1202 has previously been set so that each operation of the device can be identified. For example, The [RECIPE_START] in the first line in FIG. 12 represents a recipe execution start as indicated in the right-hand column in FIG. 12. When the device operation involves numerical data (e.g., stage movement operation), numerical values (e.g., 30000000 and 150000000 representing the moving distance or the coordinates of the destination) are recorded together with the log identification command 1202 (e.g., [STAGE_MOVE]) as shown in the sixth line in FIG. 12.

As shown in FIG. 12, the file storing the history information contains numerous pieces of information other than the monitoring items. Thus, the data analysis calculation unit searches these log data for data corresponding to a monitoring item by using a log identification command representing the monitoring item (sample type name, process name, lot ID, wafer ID, monitoring item, date/time, etc.) and thereby extracts a certain number of pieces of data necessary for the comparison of the monitoring item as the history information. The extracted data may either be stored in a separately created file or acquired each time when it is necessary by searching the history information file. By statistically processing the extracted data, the judgment criteria (average value, upper limit value, lower limit value, etc.) corresponding to the monitoring item (target of evaluation) are calculated.

The fluctuation width of each monitoring item varies since the observation condition varies from sample to sample. Thus, it is desirable to associate the value of each monitoring item with information capable of identifying the sample (type name, process name, lot ID, wafer ID, etc.) as will be illustrated later. As shown in the third line in FIG. 12, information identifying the sample is acquired at the start of the recipe execution. In this example, data "FMEM001,STIE,A0001,Slot01" has been stored in the order of type information, process information, lot ID and slot ID. Thereafter, the device operations until the storage of [WF_UNLOAD] (indicating sample withdrawal) are performed on the sample. Therefore, each piece of log data can be associated with the information of [WF_INFO] stored immediately before the log data. In cases where two or more pieces of information identifying the sample are inputted, the association may also be set with all the sample-identifying information stored between [WF_LOAD] and [WF_UNLOAD].

As described above, the defect review device in accordance with this example is capable of detecting an abnormality occurring to a part of the device more immediately compared to the review device in the first example and taking countermeasures against the abnormality without waiting until the end of the process. Therefore, it becomes possible to reduce the number of samples finishing the inspection/measurement in the abnormal state (state with the abnormality) to zero and perfectly prevent such samples from flowing to the next process. Further, quicker feedback becomes possible since the investigation on the causes of the abnormal device operation and the abnormal monitoring result is facilitated.

THIRD EXAMPLE

An example of GUIs usable for the first and second examples will be explained below.

In the above first and second examples, the explanation has been given of the early abnormality detection implemented by the monitoring/storing of the items for the judgment on the device's processing performance and the comparison of the items with the past history information. By further displaying the result of the comparison on a display unit (e.g., the monitor 17) through a GUI explained below, the operator, manager, etc. are allowed to easily recognize the abnormalities of the device.

An example of the setting of the monitoring judgment conditions, the displaying of data, and the displaying the alert on the GUI will be described below referring to FIGS. 13-18. In FIG. 13, the operator selects whether to set the judgment conditions for the monitoring result or to make the device display data of previous monitoring results, by selecting the button 1301 or the button 1302 on the GUI 1300.

When the judgment condition setting button 1301 is selected, the GUI 1400 shown in FIG. 14 is displayed on the screen. On this GUI 1400, the operator can make detailed settings in regard to observation sample information which is acquired concomitantly at the start of the review sequence, such as the type name 1401 of the product, the process name 1402, the lot ID 1403 and the wafer ID 1404. Since the fluctuation width of the value of each monitoring item explained in the first and second examples can vary depending on the sample type, the above setting of the judgment conditions for each sample type makes it possible to perform the abnormality judgment with appropriate conditions even when the type of the observed sample changes.

In the next area 1405, the operator sets the monitoring item together with a management number (No.). When there are two or more monitoring items as in the second example, the fluctuation width from the past history records can vary depending on the monitoring item. Therefore, it is desirable to set the judgment criteria for each monitoring item as in this example.

Subsequently, the operator sets a condition for the selection of judgment data to be used for the comparison (latest data, moving average, etc.) in the area 1406 and thereafter sets arbitrary values or judgment reference values based on the standard deviation in the area 1407. When the "ARBITRARY" is selected, the operator inputs an upper limit reference value and a lower limit reference value in the setting boxes UCL (Upper Control Limit) and LCL (Lower Control Limit). The judgment method shown here is just an example, and thus the method can also include settings based on various statistical quality control methods, such as the process capability index (Cp, Cpk) and a certain tendency. It is possible to employ multiple judgment algorithms in combination and issue the alert when the device is judged to have an abnormality by all the algorithms (or by two or more algorithms) or by any one of the algorithms. By allowing the operator to select the data used for the judgment and the judgment algorithm(s) as in this example, more flexible judgment criteria can be set.

Further, in the area 1408, the operator can arbitrarily specify the contents of the alert message (which is issued when the monitoring item is off the judgment reference range) together with a management number (CODE). When there are two or more monitoring items, registering the alert message for each monitoring item helps the operator to easily recognize the abnormal part (to which the abnormality has occurred) and the cause of the abnormality.

The operator can register, cancel, or modify (RETURN button) the above settings by pressing one of the buttons 1409.

Figure 15:
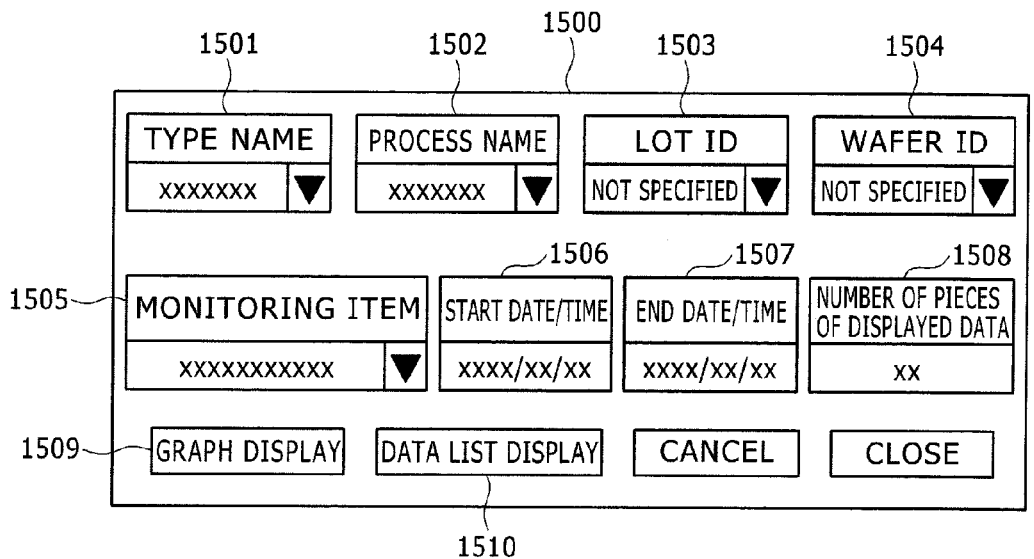
FIG. 15 is a schematic diagram showing an example of a screen for setting data display conditions in accordance with the present invention.

When the data display button 1302 is selected on the GUI 1300 shown in FIG. 13, the GUI 1500 shown in FIG. 15 is displayed. The GUI 1500 is a screen for selecting the data to be displayed and the display format. Also on this GUI 1500, the operator can make detailed settings in regard to the observation sample information which is acquired concomitantly at the start of the review sequence, such as the type name 1501 of the product, the process name 1502, the lot ID 1503 and the wafer ID 1504. Subsequently, the operator specifies the monitoring item 1505 to be displayed, the start date/time 1506 and the end date/time 1507 of the data period, and the number 1508 of pieces of data to be displayed. After setting the above conditions, the operator selects the display method such as graph display 1509 or data list display 1510.

Figure 16:
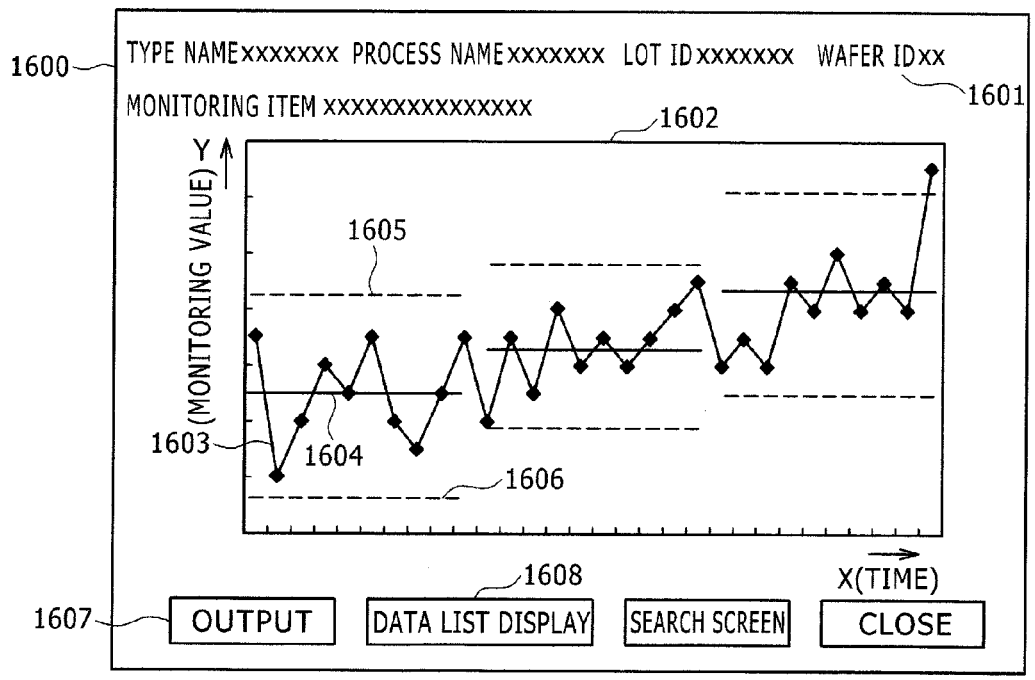
FIG. 16 is a schematic diagram showing an example of a screen for graph display of data in accordance with the present invention.

When the graph display 1509 is selected on the GUI 1500 shown in FIG. 15, the GUI 1600 shown in FIG. 16 is displayed. On the GUI 1600, the graph 1602 plotting data corresponding to the conditions set on the GUI 1500 is displayed. The conditions set on the GUI 1500 are displayed in the area 1601. It is also possible to let the operator select the items (type name, monitoring item, etc.) in the area 1601 and directly change the display target data not through the GUI 1500. While the transition of the selected past history records is indicated with a polygonal line 1603 in the graph 1602, other types of graphs (e.g., bar graph) may also be used as needed. The X-axis of the graph represents the monitoring time and the Y-axis represents the monitoring value (monitored value). In the graph, the judgment data 1406 which have been set on the GUI 1400 shown in FIG. 14, the data average value 1604 calculated based on the judgment reference value 1407, the UCL 1605 and the LCL 1606 are displayed, allowing the operator to check the transition of the data and the status of the judgment. In addition to the direct output (display) of the graph on the review device 4 as a report, the graph can be converted into various types of electronic data loadable into other devices and outputted to other systems via the network 7, etc. by pressing the button 1607.

When the data list display button 1510 or 1608 is selected on the GUI 1500 or 1600, the GUI 1700 shown in FIG. 17 is displayed. On this GUI 1700, a list 1701 including the result for each monitoring value and accompanying information is displayed. Similarly to the graph 1602, the displayed result can be converted into various types of electronic data and outputted to other systems via the review device 4, the network 7, etc. The operator can switch among the GUIs 1500, 1600 and 1700 as needed.

When a monitoring value exceeded the criterion, the GUI 1800 shown in FIG. 18 is displayed. On this GUI 1800, the date/time 1801 of exceeding the criterion, the No. 1802 representing the monitoring item, the CODE 1803 as the management number of the alert message, and the alert message 1804 are displayed in list display together with history records of alerts that occurred in the past. By the display of the current alert together with the history records of alerts occurring in the past, the operator is allowed to check the frequency of occurrence of the alert occurring this time and the date/time of the latest occurrence of a similar alert, which is helpful in taking countermeasures against the abnormality. This displayed result can also be converted into various types of electronic data and outputted to other systems via the review device 4, the network 7, etc. by pressing the button 1805.

The GUIs explained above (FIGS. 13-18) allows the operator to easily recognize the abnormality detected by the device, and thus countermeasures against the abnormality can be taken immediately.

Incidentally, the GUI display is not restricted to the styles illustrated in this example; any type of GUI display may be employed as longs as the operator can compare the present operating status of the device with the past history records.

It is desirable to display these GUIs not only on the monitor 17 directly connected to the device but also on other devices connected via a network and a management device used for remote management. This configuration makes it possible to check abnormalities occurring in other manufacturing processes. Thus, depending on the contents of abnormality, processes can be interrupted when it is judged that other manufacturing processes can be affected. Further, countermeasures against abnormalities can be taken immediately since even a manager at a remote place can directly recognize the abnormalities.

While some examples in accordance with the present invention have been described above, the present invention is not to be restricted to the particular illustrative examples. It is understandable to those skilled in the art that a variety of modifications are possible within the scope of the present invention described in the appended claims.

DESCRIPTION OF REFERENCE CHARACTERS

1 data management server
2 manufacturing device
3 inspection device
4 review device
5 analysis device
6 review/analysis device
7 network
8 imaging device
9 electron source
10, 11 condenser lens
12 deflection scanning coil
13, 14 objective lens
15 stage
16 storage device
17 monitor
18 input device
19 control unit
20 image calculation unit
21 A/D conversion unit
22 electronic optical system control unit
23 stage control unit
24 high-voltage stabilized power supply
25 detector
26 data analysis calculation unit
701 chip
702 filament current value
703, 704 voltage value
705 acceleration voltage value
706 probe current control electrode
707 extraction electrode
708 control electrode
709 acceleration electrode
801 visual field
802 center coordinates
803 reference point of an alignment mark
901, 902 alignment pattern
903 ideal stage XY axes
904 XY axes recognized by alignment
1001 reference image
1002 defect image
1003 image processing result
1004 high-magnification image
1005 defect detection coordinates
1006 visual field center coordinates
1101 electron beam
1102 excitation coil
1103 magnetic field
1104 wafer
1105 focal point
1106 control range
1107 applied electric current
1108 focal point before the control
1201 log data output date/time
1202 log identification command
1203 input/output data
1300, 1400, 1500, 1600, 1700, 1800 GUI
1602 graph
1603 polygonal line
1604 data average value
1605 UCL
1606 LCL

The invention claimed is:

1. A charged particle beam device which executes a sequence of automatically acquiring images of multiple parts of a sample mounted on a sample table by irradiating the multiple parts with a primary charged particle beam, comprising:
   imaging means which acquires the images; and
   control means which controls the imaging means,
   wherein the control means compares a value of a monitoring item of the imaging means set or calculated at the time of the execution of the sequence with history information on the monitoring item and thereby detects an occurrence of a detection error of a defect coordinate or an oversight of a defect by obtaining fluctuation of the monitoring item with respect to the history information.

2. The charged particle beam device according to claim 1, comprising display means which displays temporal transition of the fluctuation.

3. The charged particle beam device according to claim 2, wherein an alert is issued on the display means when the width of the fluctuation exceeds a prescribed threshold value.

4. The charged particle beam device according to claim 3, wherein a setting screen to be used for setting the method of the comparison with the threshold value or the history information is displayed on the display means.

5. The charged particle beam device according to claim 1, comprising a sample stage which moves the sample table,
wherein a control parameter related to alignment of the irradiating position of the primary charged particle beam is used as the monitoring item.

6. The charged particle beam device according to claim 5, wherein the amount of offset or rotation with respect to a reference position of the primary charged particle beam irradiating position is used as the monitoring item.

7. The charged particle beam device according to claim 1, wherein:
the imaging means executes two-step imaging for the acquisition of the image, in which an image is captured at a first magnification ratio and then the visual field center for imaging at a second magnification ratio higher than the first magnification ratio is determined by using the image captured at the first magnification ratio, and
a control parameter related to the imaging at the first magnification ratio or the second magnification ratio is used as the monitoring item.

8. The charged particle beam device according to claim 7, wherein automatic focusing accuracy in the imaging or a success rate of the imaging at the second magnification ratio is used as the monitoring item.

9. A defect observation device which executes a sequence of automatically acquiring an image of a defect position of a prescribed sample by irradiating the defect position with a primary charged particle beam by using defect position information on the sample acquired by an external inspection device, comprising:
imaging means which acquires the image; and
control means which controls the imaging means,
wherein the control means compares a value of a monitoring item of the imaging means set or calculated at the time of the execution of the sequence with history information on the monitoring item and thereby detects an occurrence of a detection error of a defect coordinate or an oversight of a defect by obtaining fluctuation of the monitoring item with respect to the history information.

10. The defect observation device according to claim 9, comprising storage means which stores recipe information to be used for controlling the execution of the sequence,
wherein the control means executes the calculation of the fluctuation after setting values of monitoring items based on the recipe information.

11. The defect observation device according to claim 9, comprising sample storage means which stores a plurality of samples,
wherein the calculation of the fluctuation is executed after the sequence for one sample stored in the sample storage means is finished.

12. A management server which is capable of being connected via a communication line to a charged particle beam device that executes a sequence of automatically acquiring images of multiple parts of a sample conveyed from sample storage means storing a plurality of samples by irradiating the multiple parts with a primary charged particle beam, comprising:
storage means which stores history information on a monitoring item of the charged particle beam device set or calculated at the time of the execution of the sequence; and
calculation means which compares a value of the monitoring item set or calculated for the sample with the history information and thereby detects an occurrence of a detection error of a defect coordinate or an oversight of a defect by obtaining fluctuation of the monitoring item with respect to the history information.

* * * * *